United States Patent

Kakimizu et al.

[11] Patent Number: 5,552,423
[45] Date of Patent: Sep. 3, 1996

[54] ISOTHIAZOLONE DERIVATIVE AND MICROBICIDAL COMPOSITION COMPRISING THE SAME AS ACTIVE INGREDIENT

[75] Inventors: Akiko Kakimizu, Nishinomiya; Kenji Arai, Toyonaka; Norio Kimura; Tomohiro Teramae, both of Takarazuka, all of Japan

[73] Assignee: Sumitomo Chemical Company, Limited, Osaka-fu, Japan

[21] Appl. No.: 312,962

[22] Filed: Sep. 30, 1994

[30] Foreign Application Priority Data

Oct. 1, 1993 [JP] Japan ................................... 5-246639

[51] Int. Cl.⁶ ...................... C07D 275/03; A01N 43/72
[52] U.S. Cl. ............................ 514/372; 548/213
[58] Field of Search ............................ 548/213; 514/372

[56] References Cited

U.S. PATENT DOCUMENTS 3,761,488  9/1973  Lewis et al. .
4,105,431  8/1978  Lewis et al. .
4,127,687  11/1978  Dupont .

Primary Examiner—Robert Gerstl
Attorney, Agent, or Firm—Birch, Stewart, Kolasch & Birch, LLP

[57] ABSTRACT

There is disclosed a novel isothiazolone derivative of the formula:

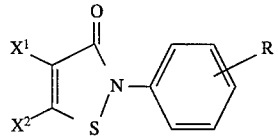

wherein $X^1$ and $X^2$ are the same or different and are independently hydrogen, chlorine or bromine; and R is haloalkoxy. The isothiazolone derivative is effective as a microbicide. Also disclosed are a microbicidal composition containing the isothiazolone derivative as an active ingredient, and an intermediate compound for use in the production of the isothiazolone derivative.

6 Claims, No Drawings

ISOTHIAZOLONE DERIVATIVE AND MICROBICIDAL COMPOSITION COMPRISING THE SAME AS ACTIVE INGREDIENT

FIELD OF THE INVENTION present invention relates to a novel isothiazolone derivative and a microbicidal composition comprising the isothiaolone derivative as an active ingredient. The present invention also relates to an intermediate compound for use in the production of the isothiazolone derivative.

BACKGROUND OF THE INVENTION

There are disclosed some isothiazolone derivatives in the U.S. Pat. Nos. 3,761,488 and 4,127,687. These isothiazolone derivatives do not have satisfactory effects of preventing or inhibiting the growth of microorganisms such as bacteria and fungi.

SUMMARY OF THE INVENTION

The present inventors have intensively studied to develop a novel microbicide, which can prevent various troubles caused by microorganisms. As a result, they have found that particular isothiazolone derivatives have excellent effects of destroying or inhibiting microorganisms, thereby completing the present invention.

Thus, the present invention provides an isothiazolone derivative of the formula:

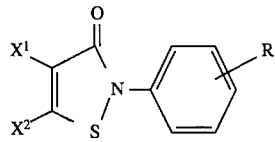

wherein $X^1$ and $X^2$ are the same or different and are independently hydrogen, chlorine or bromine;. and R is haloalkoxy. The present invention also provides a microbicidal composition comprising the isothiazolone derivative (I) as an active ingredient and an intermediate compound for use in the production of the isothiazolone derivative (I).

DETAILED DESCRIPTION OF THE INVENTION

In the isothiazolone derivative (I), the substituent R is haloalkoxy, usually $C_1$–$C_8$ haloalkoxy, and preferably $C_1$–$C_4$ haloalkoxy. Typical examples of the haloalkoxy are fluoroalkoxy such as difluoromethoxy, trifluoromethoxy, chlorodifluoromethoxy, pentafluoroethoxy and 1,1,2,2-tetrafluoroethoxy.

The isothiazolone derivative (I) of the present invention has excellent microbicidal activity against various microorganisms including the following bacteria and fungi.

Bacteria:

Genera of Bacillus, Clostridium, Enterococcus, Flavobacterium, Klebsiella, Micrococcus, Proteus, Pseudomonas, Escherichia, Staphylococcus, Desulphovibrio, Enterobacter, Achrcmobacter, Cellulomonas, Paracolabactrum, Sphaerotilus, Sporocytophage, Gallionella, Leptothrix, Beggiatoa and Aerobacter.

Fungi:

Genera of Aspergillus, Penicillium, Cladosporium, Aureobasidium, Tyromyces, Coriolus, Myrothecium, Fusarium, Rhizopus, Mucor, Epicoccum, Trichoderma, Phoma, Geotrichum and Monilia.

The isothiazolone derivative of the formula (I) wherein $X^1$ is hydrogen can be prepared by reacting a disulfide of the formula (II):

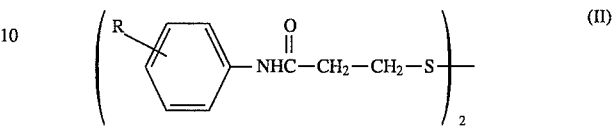

wherein R is as defined above, with a halogenating agent. The isothiazolone derivative of the formula (I) wherein $X^1$ is chlorine or bromine can be prepared by reacting the isothiazolone derivative of the formula (I) wherein $X^1$ is hydrogen, with a halogenating agent.

The above reaction is usually carded out in the presence or absence of a solvent at a temperature of 0° to 150° C. for a period of 1 to 24 hours. The halogenating agent is used in an amount of 1 to 10 equivalents to one equivalent of the disulfide (II) or the isothiazolone derivative of the formula (I) wherein $X^1$ is hydrogen.

Typical examples of the halogenating agent are chlorine gas, sulfuryl chloride, bromine, N-chlorosuccinimide and N-bromosuccinimide.

Examples of the solvent are aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloroethane, chlorobenzene and dichlorobenzene; ketones such as acetone, methyl ethyl ketone, methyl isobutyl ketone, isophorone and cyclohexanone; fatty acids such as formic acid, acetic acid and oleic acid; alcohols such as methanol, ethanol, isopropanol, t-butanol, octanol, cyclohexanol, methyl cellosolve, diethylene glycol and glycerin; esters such as ethyl formate, ethyl acetate, butyl acetate and diethyl carbonate; nitro compounds such as nitroethane and nitrobenzene; nitriles such as acetonitrile and isobutyronitrile; tertiary amines such as pyridine, methylamine, N,N-diethyianfline, tributylamine and N-methyl morpholine; acid amides such as formamide, N,N-dimethylformamide and acetamide; and sulfur compounds such as dimethyl sulfoxide and sulfolane. These solvents can be used alone or in combination.

After completion of the reaction, the reaction mixture is subjected to an ordinary post-treatment such as organic solvent extraction and concentration. When sulfuryl chloride is used as the halogenating agent, a saturated aqueous solution of sodium hydrogen carbonate may be added to the reaction mixture, if necessary, before the organic solvent extraction and concentration. The reaction product may be purified, if necessary, by a purification procedure such as chromatography, distillation or recrystallization. Thus, the isothiazolone derivative (I) of the present invention can be obtained.

Typical examples of the isothiazolone derivative (I) which can be prepared in this manner are shown in Table 1; these examples are, however, to be construed as merely illustrative, and not limitations of the present invention in any way whatsoever.

TABLE 1

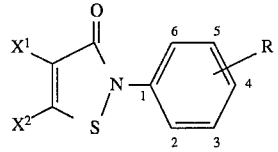

| Compound No. | X¹ | X² | R |
|---|---|---|---|
| (1) | H | H | 2-OCF$_3$ |
| (2) | H | H | 3-OCF$_3$ |
| (3) | H | H | 4-OCF$_3$ |
| (4) | H | H | 2-OCF$_2$H |
| (5) | H | H | 3-OCF$_2$H |
| (6) | H | H | 4-OCF$_2$H |
| (7) | H | H | 2-OCF$_2$CF$_2$H |
| (8) | H | H | 3-OCF$_2$CF$_2$H |
| (9) | H | H | 4-OCF$_2$CF$_2$H |
| (10) | H | H | 4-OCF$_2$Cl |
| (11) | Cl | Cl | 2-OCF$_3$ |
| (12) | Cl | Cl | 3-OCF$_3$ |
| (13) | Cl | Cl | 4-OCF$_3$ |
| (14) | Cl | Cl | 2-OCF$_2$H |
| (15) | Cl | Cl | 3-OCF$_2$H |
| (16) | Cl | Cl | 4-OCF$_2$H |
| (17) | Cl | Cl | 2-OCF$_2$CF$_2$H |
| (18) | Cl | Cl | 3-OCF$_2$CF$_2$H |
| (19) | Cl | Cl | 4-OCF$_2$CF$_2$H |
| (20) | Cl | Cl | 4-OCF$_2$Cl |
| (21) | H | Cl | 2-OCF$_3$ |
| (22) | H | Cl | 3-OCF$_3$ |
| (23) | H | Cl | 4-OCF$_3$ |
| (24) | H | Cl | 2-OCF$_2$H |
| (25) | H | Cl | 3-OCF$_2$H |
| (26) | H | Cl | 4-OCF$_2$H |
| (27) | H | Cl | 2-OCF$_2$CF$_2$H |
| (28) | H | Cl | 3-OCF$_2$CF$_2$H |
| (29) | H | Cl | 4-OCF$_2$CF$_2$H |
| (30) | H | Cl | 4-OCF$_2$Cl |
| (31) | Cl | H | 2-OCF$_3$ |
| (32) | Cl | H | 3-OCF$_3$ |
| (33) | Cl | H | 4-OCF$_3$ |
| (34) | Cl | H | 2-OCF$_2$H |
| (35) | Cl | H | 3-OCF$_2$H |
| (36) | Cl | H | 4-OCF$_2$H |
| (37) | Cl | H | 2-OCF$_2$CF$_2$H |
| (38) | Cl | H | 3-OCF$_2$CF$_2$H |
| (39) | Cl | H | 4-OCF$_2$CF$_2$H |
| (40) | Cl | H | 4-OCF$_2$Cl |
| (41) | Br | Br | 2-OCF$_3$ |
| (42) | Br | Br | 3-OCF$_3$ |
| (43) | Br | Br | 4-OCF$_3$ |
| (44) | Br | Br | 2-OCF$_2$H |
| (45) | Br | Br | 3-OCF$_2$H |
| (46) | Br | Br | 4-OCF$_2$H |
| (47) | Br | Br | 2-OCF$_2$CF$_2$H |
| (48) | Br | Br | 3-OCF$_2$CF$_2$H |
| (49) | Br | Br | 4-OCF$_2$CF$_2$H |
| (50) | Br | Br | 4-OCF$_2$Cl |

The disulfide (II) which is an intermediate compound for use in the production of the isothiazolone derivative (I) can be prepared through the following pathway:

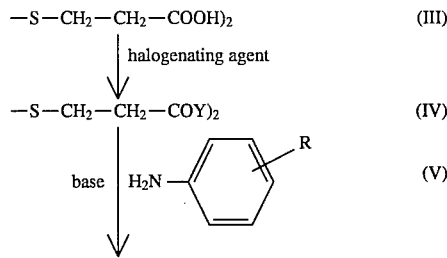

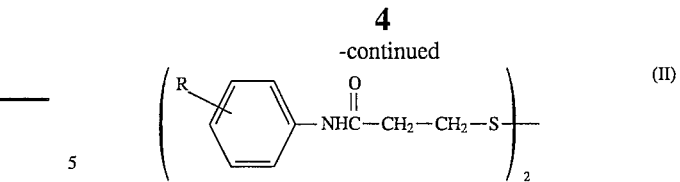

wherein Y is halogen and R is as defined above.

That is, 3,3'-dithiopropionic acid (III) is halogenated with a halogenating agent to give an acid halide (IV), which is then reacted with aniline derivative (V) in the presence of a base to give the desired disulfide (II).

The respective steps will hereinafter be explained in detail.

Step 1: Halogenation of 3,3'-dithiopropionic acid (Ill) into acid halide (IV)

The reaction is usually carried out in a solvent and, if necessary, in the presence of a catalyst, at a temperature of 0° to 150° C. for a period of 0.5 to 20 hours. Examples of the halogenating agent are thionyl chloride, phosphorus pentachloride, phosphorus trichloride and phosgene. Examples of the catalyst are pyridine, triethylamine and N,N-dimethylformamide. The halogenating agent and catalyst are used in amounts of 2 to 5 equivalents and 0.05 to 0.25 equivalent, respectively, to one equivalent of 3,3'-dithiopropionic acid (III).

Step 2: Reaction of acid halide (IV) with aniline derivative (V) to give disulfide (II)

The reaction is usually carried out in a solvent and in the presence of a base at a temperature of 0° to 150° C. for a period of 1 to 24 hours. Examples of the base are inorganic bases such as sodium hydroxide, potassium hydroxide and potassium carbonate; and organic bases such as triethylamine and pyridine. The aniline derivative (V) and the base are used in amounts of 2 to 2.2 equivalents and 2 to 3 equivalents, respectively, to one equivalent of the acid halide (IV).

Typical examples of the solvent which can be used in steps 1 and 2 are aliphatic hydrocarbons such as hexane, heptane, ligroin and petroleum ether; aromatic hydrocarbons such as benzene, toluene and xylene; halogenated hydrocarbons such as chloroform, dichloroethane, chlorobenzene and dichlorobenzene; ethers such as diethyl ether, diisopropyl ether, dioxane, tetrahydrofuran and diethylene glycol dimethyl ether; esters such as ethyl formate, ethyl acetate, butyl acetate and diethyl carbonate; nitro compounds such as nitroethane and nitrobenzene; nitriles such as acetonitrile and isobutyronitrile; acid amides such as formamide, N,N-dimethylformamide and acetamide; and sulfur compounds such as dimethyl sulfoxide and sulfolane. These solvents can be used alone or in combination. In step 2, water may be added to the reaction system for double phase reaction.

After completion of the reaction in step 1, the reaction mixture is subjected to an ordinary post-treatment such as removal of the solvent. The acid halide (IV) may be isolated, if necessary, by distilling or purifying the reaction product. Alternatively, the reaction mixture obtained in step 1 may be used directly for the reaction in step 2.

After completion of the reaction in step 2, the reaction mixture is subjected to an ordinary post-treatment such as removal of the solvent, extraction with a solvent and concentration, followed by, if necessary, depositing crystals with the addition of aqueous hydrochloric acid and washing the crystals with water. The disulfide (II) may be isolated, if necessary, by purifying the reaction product by chromatography or recrystallization.

Typical examples of the disulfide (II) which can be prepared in this manner are shown in Table 2; these examples are, however, to be construed as merely illustrative, and not limitations of the present invention in any way whatsoever.

TABLE 2

$$\left( \underset{\text{R}}{\underset{\|}{\bigcirc}} - \text{NHC} - \text{CH}_2 - \text{CH}_2 - \text{S} \right)_2$$

| Compound No. | R |
|---|---|
| (101) | 2-OCF$_3$ |
| (102) | 3-OCF$_3$ |
| (103) | 4-OCF$_3$ |
| (104) | 2-OCF$_2$H |
| (105) | 3-OCF$_2$H |
| (106) | 4-OCF$_2$H |
| (107) | 2-OCF$_2$CF$_2$H |
| (108) | 3-OCF$_2$CF$_2$H |
| (109) | 4-OCF$_2$CF$_2$H |
| (110) | 4-OCF$_2$Cl |

When used as an active ingredient of microbicidal compositions, the isothiazolone derivative (I) of the present invention can be in any possible form. The isothiazolone derivative (I) may be used as such or diluted with water, an organic solvent, a powdery substance or other appropriate carriers. Alternatively, the isothiazolone derivative (I) may be mixed with an appropriate liquid or solid carrier and prepared into various formulations such as wettable powders, liquid formulations, emulsifiable concentrates, dusts, granules or fine granules by a conventional method for preparation of microbicides. If necessary, wetting agents, dispersing agents, emulsifiers, lubricants and other auxiliary agents may be added to these formulations.

Each formulation contains the isothiazolone derivative (I) as an active ingredient in an amount of 1% to 99% by weight, preferably 10% to 90% by weight, based on the total weight of the formulation.

The liquid carrier used for formulation should serve as a solvent of the isothiazolone derivative (I) or should be able to disperse or dissolve the isothiazolone derivative (I) with the aid of auxiliary agents. Examples of the liquid carrier are water, methanol and dimethyl sulfoxide. Examples of the solid carrier are silica gel, diatomaceous earth, alumina, talc, calcium carbonate and clay. Typical examples of the auxiliary agent are acetone and hexane.

When used as an active ingredient of microbicidal compositions, the isothiazolone derivative (I) can be contained at an appropriate concentration which is determined depending upon the properties of target microorganisms. The optimum concentration can be determined by systematic examinations. In general, the desirable concentration of the isothiazolone derivative (I) is 0.01 to 100,000 ppm, based on the weight of a material to be protected.

The microbicidal composition containing the isothiazolone derivative (I) of the present invention as an active ingredient is useful for preventing or inhibiting the growth of microorganisms in industrial fields, especially.

The present invention will be further illustrated by the following Production Examples, Reference Example and Test Example, which are to be construed as merely illustrative, and not limitations of the present invention in any way whatsoever. The respective compounds are designated by the corresponding numbers shown in Tables 1 and 2.

Production Example 1

Preparation of compounds (3) and (23)

First, 18.73 g of N,N'-di(4-trifluoromethoxyphenyl)-3,3'-dithiopropionamide was suspended in 200 ml of toluene, after which 23.92 g of sulfuryl chloride was then added dropwise to the suspension at room temperature, and the resultant mixture was stirred for 12 hours. After completion of the reaction, the reaction mixture was concentrated, and 250 ml of a saturated aqueous solution of sodium hydrogencarbonate was added to the concentrate with taking care to prevent foaming. The product was extracted with ethyl acetate. The organic layer was washed with water, dried with magnesium sulfate, and concentrated. The concentrate was purified by column chromatography (hexane: ethyl acetate= 3:1 to 1:1) to give 6.4 g of 2-(4-trifluoromethoxyphenyl)-4-isothiazolin-3-on (compound (3); m.p., 117°–118° C.) and 5.1 g of 2-(4-trifluoromethoxyphenyl)-5-chloro-4-isothiazolin-3-on (compound (23); m.p., 51°–52° C.)

Production Example 2

Preparation of compound (13)

First, a mixture containing 6.4 g of 2-(4-trifluoromethoxyphenyl)-4-isothiazolin-3-on and 5.1 g of 2-(4-trifluoromethoxyphenyl)-5-chloro-4-isothiazolin-3-on was suspended in 100 ml of dichloromethane, after which 19 g of sulfuryl chloride was then added dropwise to the suspension dropwise at room temperature, and the resultant mixture was stirred for 12 hours. After completion of the reaction, 200 ml of a saturated aqueous solution of sodium hydrogencarbonate was added to the reaction mixture, and the dichloromethane layer was separated. The aqueous layer was extracted with 150 ml of dichloromethane. The combined dichloromethane layer was washed with water, dried with magnesium sulfate, and concentrated. The concentrate was purified by column chromatography (hexane: ethyl acetate= 6:1) to give 4 g of 2-(4-trifluoromethoxyphenyl)-4,5-dichloro-4-isothiazolin-3-on (compound (13); m.p., 129°–130° C.).

Production Example 3

Preparation of compound (103)

First, a mixture containing 100 g of p-trifluoromethoxyaniline, 700 ml of toluene and 98.2 g of pyridine was cooled to 0° C., after which 69.7 g of 3,3'-dithiopropionic acid dichloride were added dropwise to the mixture, and the resultant mixture was stirred at room temperature (approximately 20° C.) for 1 hour and then at 80° C. for 2 hours. After completion of the reaction, the solvent was removed from the reaction mixture, and 500 ml of a 5% aqueous solution of hydrochloric acid was added to the residue for crystallization, and the deposited crystals were collected by filtration. The crystals were washed with water and dried under reduced pressure to give 160.3 g of N,N'-di(4-trifluoromethoxyphenyl)-3,3'-dithiopropionamide.

$^1$H-NMR (CDCl$_3$-DMSO-d$^6$) δ (ppm): 10.3 (brs, 2H), 7.7 (d, 4H), 7.1 (d, 4H), 2.9 (m, 8H)

IR (KBr): 3310 cm$^{-1}$, 1661 cm$^{-1}$

Reference Example 1

Preparation of 3,3'-dithiopropionic acid dichloride

First, 100 g of 3,3'-dithiopropionic acid was added to 500 ml of toluene, after which 2.5 ml of N,N-dimethylformamide was added to the mixture and 135.5 g of thionyl chloride was then added dropwise to the mixture, the resultant mixture was stirred at 50° C. for 2 hours. After completion of the reaction, the toluene was removed from the reaction mixture, which gave 122 g of 3,3'-dithiopropionic acid dichloride as a brown liquid.

$^1$H-NMR (CDCl$_3$) δ (ppm): 3.3 (4H, t), 3.0 (4H, t)
IR (neat): 1800 cm$^{-1}$ Test Example 1

Each test compound was dissolved in dimethyl sulfoxide, and the solution was mixed with potato dextrose agar (PDA) so as to have a predetermined concentration. Various fungi were independently inoculated on the compound-containing PDAs and cultured at 27° C. for 5 days, after which the growth of the fungi was evaluated. The results are shown in Table 3, as the minimum inhibitory concentration (M.I.C.) in ppm against each species of the fungi tested.

TABLE 3

| Compound No. | Fungi tested* | | | | | | |
|---|---|---|---|---|---|---|---|
| | Aa | An | Ap | Cc | Pf | Cg | Fo |
| (3) | 4 | 4 | 4 | 4 | 4 | 4 | 20 |
| (13) | 4 | 4 | 4 | 4 | 4 | 4 | 4 |

*Aa: *Alternaria alternata*
An: *Aspergillus niger*
Ap: *Aureobasidium pullulans*
Cc: *Cladosporium cladosporioides*
Pf: *Penicillium funiculosum*
Cg: *Chaetomium globosum*
Fo: *Fusarium oxysporum*

Test Example 2

Each test compound was dissolved in dimethyl sulfoxide, and the solution was mixed with an LB liquid medium so as to have a predetermined concentration. Various bacteria were independently inoculated in the compound-containing liquid media and cultured with shaking at 30° C. for 1 day, after which the growth of the bacteria was evaluated. The results are shown in Table 4, as the minimum inhibitory concentration (M.I.C.) in ppm against each species of the bacteria tested.

TABLE 4

| Compound No. | Bacteria tested* | | | | |
|---|---|---|---|---|---|
| | Bs | Cb | Fa | Ml | Sa |
| (3) | <0.08 | 0.4 | 2.0 | 2.0 | 2.0 |
| (13) | 0.4 | <0.08 | <0.08 | <0.08 | <0.08 |

*Bs: *Bacillus subtilis*
Cb: *Clostoridium butyrcum*
Fa: *Flavobacterium aquatile*
Ml: *Micrococcus luteus*
Sa: *Staphylococcus aureus*

Test Example 3

In sterile distilled water containing the test compound or reference compound at a predetermined concentration was inoculated bacteria (Pseudomonas fluorescens) at a concentration of 10$^6$ cfu/ml, and the bacterial suspension was shaken (170 rpm) at 30° C. After 4 and 8 hours from the treatment, part of the bacterial suspension was taken and inoculated on an LB agar medium with a spiral plater, followed by stationary cultivation at 30° C. for 2 days. The viable cell count (cfu/ml) was measured for the determination of bactericidal rates. The results are shown in Table 5. The bactericidal rate (%) was determined by the following equation.

$$\text{Bactericidal rate} = 100 - \frac{\text{Viable cell count in treated division}}{\text{Viable cell count in non-treated division}} \times 100$$

TABLE 5

| Compound No. | Concentration (ppm) | Bactericidal rates | |
|---|---|---|---|
| | | after 4 hours | after 8 hours |
| (13) | 1 | 53 | >99 |
| Ref Compd.*) | 1 | 27 | 23 |

*)The reference compound is of the formula:

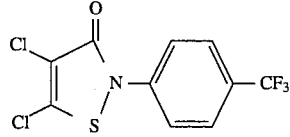

As described above, the isothiazolone derivative (I) of the present invention has excellent effects of destroying or inhibiting microorganisms such as bacteria and fungi. In particular, such effects are satisfactory at the initial stage and sustainable for a long period of time. Thus, the isothiazolone derivative (I) of the present invention can find a wide variety of applications as a microbicide.

What is claimed is:

1. An isothiazolone derivative of the formula:

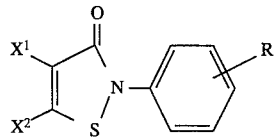

wherein $X^1$ and $X^2$ are the same or different and are independently hydrogen, chlorine or bromine; and R is haloalkoxy.

2. An isothiazolone derivative according to claim 1, wherein R is fluoroalkoxy.

3. An isothiazolone derivative according to claim 1, wherein R is trifluoromethoxy.

4. An isothiazolone derivative according to any one of claims 1 to 3, wherein $X^1$ and $X^2$ are both hydrogen or chlorine.

5. A microbicidal composition comprising as an active ingredient a microbicidally effective mount of the isothiazolone derivative according to claim 1, and an inert carrier or diluent.

6. A method for destroying or inhibiting microorganisms, which comprises applying a microbicidally effective amount of the isothiazolone derivative according to claim 1 to microorganisms.

* * * * *